United States Patent [19]

Wood et al.

[11] Patent Number: 4,908,317

[45] Date of Patent: Mar. 13, 1990

[54] METAL ACCUMULATION AND POLYSACCHARIDE PRODUCTION

[75] Inventors: John M. Wood; Francis E. Engle, both of Mound, Minn.

[73] Assignee: The Regents of the University of Minnesota, Minneapolis, Minn.

[21] Appl. No.: 918,470

[22] Filed: Oct. 14, 1986

Related U.S. Application Data

[63] Continuation-in-part of Ser. No. 526,672, Aug. 24, 1983, abandoned.

[51] Int. Cl.$^4$ .................... C12N 1/12; C12N 1/00; C12P 19/00; C12P 19/04
[52] U.S. Cl. .................................. 435/262; 75/97 R; 435/72; 435/101; 435/243; 435/257
[58] Field of Search ............... 210/602; 435/257, 262, 435/243, 72, 101; 75/97 R; 42/DIG. 17

[56] References Cited

U.S. PATENT DOCUMENTS 4,371,619  2/1983  Schwartz ........................... 435/245

OTHER PUBLICATIONS

Castorday et al., (1980), Procedings of the National Academy of Sciences, vol. 78, No. 3, pp. 1700–1702.
Tuovinen et al., (1974), International Metollurgical Reviews, vol 19, pp. 21–31.
Aliotta et al., (1982), Giornale Botanico Italiano, vol. 116 (3–4), pp. 123–129.
Allen, M. B. Archiv für Microbiologic, Bd 32(1959) pp. 270–277.

Primary Examiner—Robert J. Warden
Attorney, Agent, or Firm—Frank J. Uxa, Jr.

[57] ABSTRACT

A thermophilic-acidophilic alga, strains of *Cyanidium caldarium*, is disclosed as having a very effective external uptake of metals from metal-containing aqueous media. A process is disclosed for producing at least one polysaccharide comprises contacting an acidic aqueous medium containing at least one added metal selected from the group consisting of alkali metals, alkaline earth metals, aluminum and mixtures thereof and at least one acidophilic microorganism at conditions effective for the growth of the microorganism and the production of polysaccharide by the microorganism.

11 Claims, 1 Drawing Sheet

METAL ACCUMULATION AND POLYSACCHARIDE PRODUCTION

RELATED APPLICATION

This application is a continuation in part of application Ser. No. 06/526,672 filed Aut. 24, 1983 now abandoned.

BACKGROUND OF THE INVENTION

1. Field:

This invention related generally to microorganisms, and processes employing same, having the ability to interact with metal ions found in certain aqueous media, particularly that emanating from certain mining operations.

2. Prior Art:

Certain microorganisms have been known to possess the ability to survive in acidic aqueous media and react with metallic elements and/or compounds found therein, such as the oxidation of iron by *Thiobacillus ferroxidans*.

Representative of certain patents relating to microorganisms having the ability to immobilize or otherwise interact with metallic substances are: Chakrabarty et al, U.S. Pat. No. 3,923,597, entitled "Mercury Concentration By The Use of Microorganisms"; McCready et al, U.S. Pat. No. 4,269,699, entitled Bioadsorption Alteration of Iron Sulfide Surfaces"; Stover, U.S. Pat. No. 4,108,722, entitled "Method For The Restoration Of An Underground Reservoir"; O'Connor et al, U.S. Pat. No. 3,679,397, entitled "Bacterial Leaching Process"; Pillis et al, U.S. Pat. No. 4,352,886, entitled "Process for Treating Wastewater Containing Phenolics and Microorganism Capable of Degrading Phenolics"; Korosi, U.S. Pat. No. 3,982,932, entitled "Recovery of Silver From Gelatinous Photographic Wastes"; McElroy et al, U.S. Pat. No. 3,856,913, entitled "Copper Extraction by Rapid Bacteriological Process."

Previously known microorganisms have frequently been selective as to iron or another metal. The uptake of metal has usually been by ingestion or by oxidation, such as the oxidation of ferrous ions by *Thiobacillus ferrooxidans*. The interaction of certain microorganisms with a metal-laden aqueous media may separate certain soluble metals through the reduction of such metal, e.g., copper, by ferric ions which had been produced by the oxidation of ferrous ions.

Polysaccharides are useful materials, for example, in micellar/polymer type enhanced oil recovery (EOR) processes. However, the use of polysaccharides is often limited because of the relatively high cost involved in producing these materials. Thus, a new process for polysaccharide production would clearly be advantageous.

SUMMARY OF THE INVENTION

Figure 1:
FIG. 1 is a photomicrograph of 31,000X magification illustrating external uptake of metals by a particular strain of *Cyanidium caldarium* which as been placed on deposit with the American Type Culture Collection, 12301 Parklawn Drive, Rockville, MD, and assigned the number ATCC 40080.

*Cyanidium caldarium* having the ability to fix or collect at least one metallic material, e.g., an extraordinary loading of metallic components to or at its outer surface or external cell membrane, has been invented. Further, the invention comprises the utilization of such *Cyanidium caldarium* in a process for collecting at least one metal, in particular polyvalent metal, by contacting said metal and/or one or more compounds of said metal in an aqueous, preferably an acidic aqueous, medium.

*Cyanidium caldarium* occurs naturally in various acidic hot springs in California and New Zealand. *Cyanidium caldarium* is an acidophilic-thermophilic alga.

A process for producing at least one polysaccharide has also been discovered. In one broad aspect, the present polysaccharide process comprises providing or contacting an aqueous acidic medium containing at least one added metal selected from the group consisting of alkali metals, alkaline earth metals, aluminum and mixtures thereof and at least one acidophilic microorganism at conditions effective for the growth of the microorganism and the production of polysaccharide by the microorganism. Preferably, the polysaccharide so produced is recovered from the medium, e.g., for use in a product or other process.

The present invention provides substantial advantages. For example, the presently useful acidophilic microorganisms are able to survive the acidity of the medium while collecting metal and/ or producing polysaccharide. Thus, the process can be operated in a more cost effective continuous mode taking advantage of the living microorganisms. Also, polysaccharide production is easily controlled by, for example, controlling the addition of added metal and other components included in the medium, the acidity of the medium and the conditions at which the medium is contacted. Thus, the present invention provides an effective and easily controlled process for the production of polysaccharides.

The presently useful aqueous medium comprises water, preferably liquid water. This aqueous medium is preferably substantially free of components, e.g., ions, which substantially detrimentally affect the metal collecting capabilities and/or growth and/or polysaccharide producing capabilities of the microorganisms. This aqueous medium preferably has a pH of about 4.0 or less, more preferably in the range of about 0.0 to about 4.0 and still more preferably about 1.5 to about 2.5. Particularly good results are obtained with the acidic aqueous medium at pH of about 2.0 to about 2.3.

Acidity may be supplied to the acidic aqueous medium using any acid or combination of acids which is compatible with the remainder of the aqueous medium and does not substantially detrimentally affect the presently useful microorganisms, metal collection process and/or polysaccharide production process. Examples of useful acids include sulfuric acid, sulfurous acid, nitric acid, hydrogen halides, carboxylic acids and the like and mixtures thereof. Because of cost, availability and performance considerations, the acidic aqueous medium preferably contains sulfuric acid, more preferably as the major or predominant acid component of the acidic aqueous medium.

For polysaccharide production, the acidic aqueous medium contains at least one added metal selected from the group consisting of alkali metals, especially sodium and potassium; alkaline earth metals, especially magnesium; and calcium; aluminum and mixtures thereof. Magnesium and especially aluminum are particularly preferred as added metals in the present process. Such metal or metals are preferably included in forms which are soluble in the acidic aqueous medium. For example, the metals can be provided to the acidic aqueous medium in the form of salts of the acid or acids present in the acidic aqueous medium and/or as components which are converted to such salts in the acidic aqueous medium. Sulfates are particularly preferred as the form in which the added metal or metals exist in the acidic aqueous medium prior to any metal interaction with the presently useful microorganisms.

The amount of added metal or metals present in the acidic aqueous medium is such as to facilitate the production of polysaccharide by the microorganisms. In general, the more added metal present, the more polysaccharide produced by the microorganisms. However, care should be exercised to control the amount of metal or metals added to the acidic aqueous medium. Relatively large concentrations of added metal or metals may have a substantial detrimental effect on the growth, or even survivorability, of the microorganisms present in the acidic aqueous medium. These microorganisms can be acclimated to be somewhat more tolerant of such added metals. In any event, the concentration of added metal or metals should be such as to allow growth, i.e., reproduction, of the microorganism in the acidic aqueous medium.

Without limiting the scope of the invention to any mechanism or theory of operation, some interaction between the added metal or metals and the microorganisms in the acidic aqueous medium may occur which results in the production of polysaccharide by the microorganism. In certain embodiments, e.g., when the added metal is aluminum, it is preferred that the added metal becomes complexed with, e.g., attached or fixed to the outer surface or external cell membrane of, the microorganism.

Any suitable acidophilic microorganism or combinations of such microorganisms may be employed in the present process, e.g., the present polysaccharide production process. Preferably, such microorganisms are also thermophilic. One broad class of microorganisms which have been found to be very suitable for use in the present process are acidophilic alga, in particular acidophilic-thermophilic alga. Preferably, alga of the genus *Cyanidium* are employed, with *Cyanidium caldarium* being particularly useful. Many microorganisms suitable for use in the present invention are naturally occurring. For example, *Cyanidium caldarium* occurs naturally in various acidic hot springs in California and New Zealand. *Cyanidium caldarium* is an acidophilic-thermophilic alga.

A particular strain of *Cyanidium caldarium*, which has been placed on deposit with the American Type Culture Collection and assigned the number ATCC 40080 (hereinafter referred to as *Cyanidium caldarium* ATCC 40080), is particularly useful in the instant invention. *Cyanidium caldarium*, having metals accumulating capabilities, such as *Cyanidium caldarium* ATCC 40080, can be grown at about 10° C. or less to about 70° C. or more, in particular at about 45° C., in an acidic aqueous medium, e.g., in acid mine water from a copper-nickel mine.

Naturally occurring *Cyanidium caldarium* does not have the metal collecting capabilities of the microorganisms useful in the metal collecting process of the present invention. However, such metal collecting microorganisms can be produced by a method comprising incrementally increasing the acidity of a medium containing such naturally occurring *Cyanidium caldarium*. After such incremental increases, the acidity of the medium is preferably substantially the same as or greater than the acidity of the metal-containing medium from which metal is to be collected. Preferably, the concentrations of ions of at least one polyvalent transition metal (e.g., the metal to be collected by the final microorganism) is also incrementally increased as the acidity of the medium is increased. For example, incremental increases in the concentration of acid mine water from a copper-nickel mine to a medium containing naturally occurring *Cyanidium caldarium* are effective. Preferably, the temperature of the medium during the incremental additions is within the range of about 10° C. or less to about 70° C. The medium preferably includes at least one nutrient in an amount effective to facilitate the growth of the microorganism. Of course, other techniques may be suitable to produce desired *Cyanidium caldarium*, i.e., such microorganisms having metal material collecting ability as described herein.

*Cyanidium caldarium* ATCC 40080 is a acidophilic-thermophilic alga which can be grown free of other contaminating autotrophs without having to use sterilization procedures for the acidic aqueous medium, e.g., acid-mine water medium. *Cyanidium caldarium* ATCC 40080 grows extremely well in sulfuric acid in a pH range of zero to about 4.0 and especially well at about pH 2.0, and removes metal ions from solution by precipitation at the cell surface as metal sulfides. Metal collecting strains of *Cyanidium caldarium*, such as *Cyanidium caldarium* ATCC 40080, are particularly effective in removing high concentrations of polyvalent metals such as cobalt, iron, copper, nickel, aluminum and chromium from aqueous media containing said metals, and metals generally being present as cations in association with some anion, especially the sulfate anion.

In an acidic aqueous media containing alkali metals, especially sodium and potassium, and alkaline earth meals, especially magnesium and calcium, and aluminum, one or more of these metals become attached to the *Cyanidium caldarium*, e.g., *Cyanidium caldarium* ATCC 40080, by complexing with a polysaccharide, especially galactose, produced by the microorganism.

Introduction of glucose to a medium during growth of the microorganism, e.g., *Cyanidium caldarium*, enhances, e.g., increases, the production, e.g., the generation, of one or more polysaccharides, by the microorganism, e.g., at its surface. Sugars other than glucose, e.g., such as dextrose, fructose, sucrose and the like, and carboxylic acids containing 1 to about 4 carbon atoms per molecule, especially acetic acid, may also advantageously be utilized to enhance polysaccharide production by the organism.

The polysaccharide produced by the microorganism can be recovered from the acidic aqueous medium using separation techniques, e.g., which are conventional and well known. Such techniques include filtration, precipitation, centrifugation and the like. Preferably, the polysaccharide is complexed with the microorganism and is recovered by harvesting microorganisms from the acidic aqueous medium.

For polysaccharide production, the aqueous medium is subjected to conditions effective for the growth of the microorganism and for the production of polysaccharide by the microorganism. Such conditions may vary widely depending, for example, on the components present in the acidic aqueous medium. Preferably, the temperature is in the range of about 0° C. to about 70°

C., more preferably about 15° C. to about 60° C. The total pressure to which the acidic aqueous medium is subjected may be in the range of about 0.1 atmosphere or less to about 30 atmospheres or more. Atmospheric pressure provides acceptable results in many cases. The time for which the acidic aqueous medium is subjected may be in the range of about 0.1 hour or less to about 100 hours or more.

The acidic aqueous medium may be subjected to such effective conditions in a batch, semi-batch or continuous operation.

In certain instances, the complexation of the added metal with the microorganism, e.g., the attachment of metal sulfides to the microorganism, is such that microcrystals of the metal, e.g., metal sulfides, may be readily dislodged by agitation of the system, i.e., the aqueous medium. Such removal of the metal sulfides merit the microorganism to reinstate its added metal collection or complexation mechanism and to continue to produce polysaccharide.

In a low pH, sulfuric acid containing system, sulfate anions will tend to predominate. Thus, a significant proportion of metals present in the system can be collected as sulfides. Other anions such as the nitrate ion may, however, be advantageously reduced.

*Cyanidium caldarium* grown in acid mine water, as described herein, was transferred into 1N hydrochloric acid. In such an environment, the *Cyanidium caldarium* effected a reduction of ferric ion to ferrous ion. Thus, in hydrochloric acid systems, *Cyanidium caldarium* may beneficiate certain ores.

Heterotrophic cultures of *Cyanidium caldarium* ATCC 40080 allowed to attain anaerobic conditions in the dark produce hydrogen sulfide gas quite efficiently. This suggests that the sulfide precipitation of metals can be regarded as a probable cellular detoxification mechanism.

The particular strain, e.g., *Cyanidium caldarium* grown in a medium of increasing acidity and polyvalent metal ion content, e.g., acid mine water, as described herein, utilized in the instant invention appears very effective in removal of chromium and nickel which are present in very low concentrations in many acid mine waters. These metals are known to be potential carcinogens and their selective removal from waste waters is particularly desirable. The high rate of removal of these ions is very advantageous.

Such *Cyanidium caldarium* has several advantages in the development of biotechnology for the recovery of metals from waste waters. An organism can be grown under controlled conditions satisfying both the acidophilic and thermophilic nature of the organism. Gfowth on acidic metals-containing media, e.g., acid mine waters, simply requires a source of light and, preferably, a source of usable carbon, e.g. carbon dioxide, methanol, acetic acid and the like. Quantities of carbon dioxide up to about ten percent (10%) are quite sufficient. Also, if desired minor quantities of a sugar such as glucose and a source of ammonium and/or sulfate ions may additionally be introduced to the system.

Upon the introduction of significant quantities of nutrients, especially at least one of glucose and acetic acid, metal collecting *Cyanidium caldarium*, e.g., *Cyanidium caldarium* ATCC 40080, produces substantial quantities of polysaccharides at its surface. A medium containing a significant concentration of such organism may become a gelatinous pseudo-plastic mass.

Cultures of the *Cyanidium caldarium* ATCC 40080 microorganism are very stable with inocula having a shelf life in excess of twelve months. Sterile microbiological techniques need not be used in growing the organism in continuous culture.

The *Cyanidium caldarium* microorganism useful as a metal collector in this invention is also particularly effective in various types of processing techniques inasmuch as the metal holding ability of the microorganism appears to be independent of the viability of the strain. That is, dead or moribund such *Cyanidium caldarium* appears essentially as effective in tying up metallic ions as the viable microorganism. Thus, the microorganisms may be placed in an aqueous medium having various metallic ions desired to be removed. After collection of metals by microorganisms present, the aqueous medium is passed through a filter press or other means for separating solid materials such as the metal-laden microorganism from the aqueous medium. The microorganisms may then be rendered non-viable in removing the metals. Alternately, the live microorganisms can be processed, e.g., agitated, so that the metallic materials are removed from the microorganisms and the microorganisms then recycled to aqueous media containing metallic ions for further metal collection.

Metals recovered from metal collecting *Cyanidium caldarium* strains in a reduced state, e.g., as sulfides, are in a particularly useful form for further processing inasmuch as many metallurgical processing echniques are particularly effective for handling metallic sulfides.

The following non-limiting examples illustrate certain aspects of the present invention.

A culture of *Cyanidium caldarium* isolated from the Waimangu Caldron Outlet, North Island, New Zealand, was slowly adapted to grow in acid mine water by adding ten percent increment increases of mine water to a culture grown under the conditions described by Allen, M. B. Arch. Mikrobiol. 32 270–277 (1959), the contents of said article being incorporated herein by reference.

This *Cyanidium caldarium*, identified as *Cyanidium caldarium* ATCC 40080, which grew well on culture medium consisting of unfiltered acid mine water provided with five percent carbon dioxide, was selected for utilization as a metal collector. Cell counts of cultures in the stationary phase indicated that more than double the population is obtained if the acid mine water is supplemented with one percent glucose and one percent ammonium sulfate. Table 1 presents data on the elemental metal composition of acid mine water at pH 2.1 and shows the removal efficiencies for stationary cultures of such *Cyanidium caldarium* in the presence and absence of glucose plus ammonium sulfate.

FIG. 1 is a photomicrograph of 31,000 × magnification illustrating external uptake of metals by *Cyanidium caldarium* ATCC 40080. As shown in FIG. 1, microcrystals of metal sulfides were adhering to the external cell membrane. Toxic metals such as copper, nickel, and chromium were apparently prevented from entering the cells by an extra cellular precipitation mechanism. Without limiting the scope of the invention to any one mechanism or theory of operation, it appears that this *Cyanidium caldarium* possesses a membrane-associated sulfate reductase system. Transition metals such as copper, nickel and chromium are usually present in aqueous media in an oxidized state, e.g., each being present as a soluble sulfate, which anion appears to be reduced whereby metallic sulfides adhere to the external membrane of the *Cyanidium caldarium*.

The parent strain of *Cyanidium caldarium*, when exposed to full strength acid mine water or to 1N sulfuric acid or 1N hydrochloric acid, dies quickly without exhibiting any capacity for metal collection in such an environment.

Metals recovered from the above-noted *Cyanidium caldarium* mutant strain in a reduced state, that is as sulfides, are in a particularly useful form for further processing inasmuch as many metallurgical processing techniques are particularly effective for handling metallic sulfides.

Visual observations of the acid mine water/culture media tested indicated that one or more polysaccharides were produced in the media containing calcium, magnesium, aluminum and sodium. The media including these metals and glucose produced more polysaccharides than such media without glucose. Also, the media including the other metals with and without glucose, contained little or no polysaccharides. Such polysaccharide material was particularly plentiful in the media containing aluminum.

While this invention has been described with respect to various specific examples and embodiments, it is to be understood that the invention is not limited thereto and that it can be practiced within the scope of the following claims.

| *ELEMENT | (Ppm) ACID-MINE WATER (pH 2.1) | (Ppm) CULTURE SUPERNATANT + 1% GLUCOSE + 1% $(NH_4)_2 SO_4$ + 5% $CO_2$ | % REMOVED | (Ppm) CULTURE SUPERNATANT +5% $CO_2$ | % REMOVED |
|---|---|---|---|---|---|
| Ca | 342 | 219 | 36% | 277 | 19% |
| Mg | 456 | 228 | 50% | 342 | 25% |
| Fe | 632 | 205 | 68% | 386 | 39% |
| Cu | 119 | 60.6 | 50% | 95 | 20% |
| Al | 329 | 155 | 53% | 245 | 25% |
| Cr | 1.31 | 0.31 | 76% | 0.38 | 71% |
| Na | 28.4 | 13.2 | 54% | 20.9 | 26% |
| Ni | 4.32 | 2.55 | 41% | 2.69 | 28% |
| P | 27.0 | 13.5 | 50% | 19.1 | 29% |

*Analyzed by Plasma Emmission Spectroscopy.
Cells grown for one week from 1 liter inoculum into 8 liters of acid-mine water.

The embodiments of the present invention in which an exclusive property or privilege is claimed are as follows:

1. A method for collecting at least one metal comprising contacting a metal in an aqueous medium containing said metal with metal collecting *Cyanidium caldarium* to which said metal becomes fixed to the outer surface thereof; and separating said *Cyanidium caldarium* from said metal fixed to the outer surface thereof, said metal collecting *Cyanidium caldarium* being produced by a method comprising incrementally increasing the acidity of a medium containing substantially non-metal collecting *Cyanidium caldarium*.

2. The method of claim 1 wherein said aqueous medium contains sulfuric acid.

3. The method of claim 1 wherein said *Cyanidium caldarium* is moribund.

4. The method of claim 1 wherein said metal is selected from the group consisting of polyvalent transition metals and mixtures thereof.

5. The method of claim 1 wherein said metal is selected from the group consisting of chromium, iron, nickel, copper and mixtures thereof.

6. The method of claim 1 wherein said *Cyanidium caldarium* after said metal separation is contacted with an aqueous medium containing ions of polyvalent metal.

7. Metal collecting *Cyanidium caldarium* having microcrystals of at least one metallic material adhered to its external cell membrane, said metal collecting *Cyanidium caldarium* being produced by a method comprising incrementally increasing the acidity of a medium containing substantially non-metal collecting *Cyanidium caldarium*.

8. A method for producing *Cyanidium caldarium* capable of collecting metallic material upon its external cell membrane comprising incrementally increasing the acidity of a medium containing substantially non-metal collecting *Cyanidium caldarium*; and recovering metal collecting *Cyanidium caldarium*.

9. The method of claim 8 which further comprises incrementally increasing the polyvalent metal ion concentration of said medium.

10. A method of reducing ferric ions to ferrous ions comprising contacting a hydrochloric acid and ferric ion-containing medium or a sulfuric acid and ferric ion-containing medium with metal collecting *Cyanidium caldarium*, said metal collecting *Cyanidium caldarium* being produced by a method comprising incrementally increasing the acidity of a medium containing substantially non-metal collecting *Cyanidium caldarium*.

11. *Cyanidium caldarium* ATCC 40080 microorganism.

* * * * *

UNITED STATES PATENT AND TRADEMARK OFFICE
CERTIFICATE OF CORRECTION

PATENT NO. : 4,908,317
DATED : March 13, 1990
INVENTOR(S) : Wood et al

It is certified that error appears in the above—identified patent and that said Letters Patent is hereby corrected as shown below:

Column 1, line 12; delete "related" and insert in place thereof --relates--

Column 5, line 17; delete "merit" and insert in place thereof --permit--

Column 5, line 53; delete "gfowth" and insert in place thereof --growth--

Column 6, line 29; delete "echniques" and insert in place thereof --techniques--

Signed and Sealed this

Seventh Day of May, 1991

*Attest:*

HARRY F. MANBECK, JR.

*Attesting Officer*    Commissioner of Patents and Trademarks